(12) United States Patent
Hung (10) Patent No.: US 10,537,477 B2
(45) Date of Patent: Jan. 21, 2020

(54) SNOW GOGGLE DEVICE AND COMPOSITE LENS

(71) Applicant: ASWAN INTERNATIONAL CORP., Taipei (TW)

(72) Inventor: Tzer-An Hung, Taipei (TW)

(73) Assignee: ASWAN INTERNATIONAL CORP., Taipei (TW)

( * ) Notice: Subject to any disclaimer, the term of this patent is extended or adjusted under 35 U.S.C. 154(b) by 76 days.

(21) Appl. No.: 15/975,997

(22) Filed: May 10, 2018

(65) Prior Publication Data
US 2019/0343685 A1 Nov. 14, 2019

(51) Int. Cl.
  G02C 7/10 (2006.01)
  A61F 9/02 (2006.01)
  G02C 1/06 (2006.01)
  G02B 1/18 (2015.01)
  G02B 1/14 (2015.01)

(52) U.S. Cl.
  CPC ............ *A61F 9/023* (2013.01); *G02B 1/14* (2015.01); *G02B 1/18* (2015.01); *G02C 1/06* (2013.01); *G02C 7/102* (2013.01); *G02C 2202/16* (2013.01)

(58) Field of Classification Search
  CPC ........ G02B 1/14; G02B 1/18; G02C 2202/16; G02C 7/102; A61F 9/022
  USPC ........ 351/44, 159.01, 159.24, 159.56, 159.6, 351/159.61, 159.62, 159.63, 159.64, 351/159.65, 159.66
  See application file for complete search history.

(56) References Cited

U.S. PATENT DOCUMENTS

2015/0261010 A1* 9/2015 Kudla .............. G02B 5/23
                                              351/159.61

* cited by examiner

*Primary Examiner* — Hung X Dang
(74) *Attorney, Agent, or Firm* — Li & Cai Intellectual Property (USA) Office (57) ABSTRACT

A snow goggle device includes a composite lens and a spectacle frame fastened to a periphery of the composite lens. The composite lens includes a multi-layer sheet, a protective sheet spaced apart from the multi-layer sheet, and a combining layer connecting the multi-layer sheet and the protective sheet. The multi-layer sheet includes an anti-UV layer, an anti-fog layer, and a photochromic layer, the latter two of which are respectively disposed on an inner surface and an outer surface of the anti-UV layer. The photochromic layer has an adjustable transmittance that is changed when a UV light travels through the photochromic layer. The anti-UV layer can reflect a UV light to the photochromic layer. The multi-layer sheet, the protective sheet, and the combining layer jointly define an air layer that is configured to slow down the transference of an outer temperature of the protective sheet to the multi-layer sheet.

10 Claims, 5 Drawing Sheets

SNOW GOGGLE DEVICE AND COMPOSITE LENS

BACKGROUND OF THE DISCLOSURE

Field of the Disclosure

The present disclosure relates to a snow goggle; in particular, to a snow goggle device and a composite lens.

Description of Related Art

In order to prevent the eyes from being exposed to light refracted by snow or from being directly injured by wind or snow, snow goggles can be worn for protection during activities in harsh weather. When a user wearing a snow goggle moves about in the snow, an internal temperature of the snow goggle is increased due to heat from the user, and an external temperature of the snow goggle is decreased due to the low temperature of the outer environment, such that the internal temperature and the external temperature of the snow goggle have a large difference. Accordingly, an inner surface of the snow goggle would fog up due to condensation of steam in the snow goggle, affecting the user's view.

In order to solve the above drawback, an inner surface of a conventional snow goggle can be covered by an anti-fog spray after being cleaned, thereby preventing steam from condensing onto the inner surface. However, the conventional snow goggle is inconvenient in that it needs to be cleaned before the anti-fog spray is used, and the anti-fog spray needs to be regularly sprayed on the inner surface of the conventional snow goggle.

Moreover, despite that the conventional snow goggle is provided with a photochromic layer, no optical structure for improving photochromic sensitivity is cooperated with the photochromic layer, such that the conventional snow goggle often has bad photochromic sensitivity (i.e., the photochromic layer would require a longer time to change color).

SUMMARY OF THE DISCLOSURE

The present disclosure provides a snow goggle device and a composite lens to solve the drawbacks associated with conventional snow goggles.

The present disclosure provides a snow goggle device, which includes a composite lens and a spectacle frame. The composite lens includes a multi-layer sheet, a protective sheet, and a combining layer. The multi-layer sheet is defined as an internal view region and an internal combining region that is in a ring shape and is arranged around the internal view region. The multi-layer sheet includes an anti-UV layer, an anti-fog layer, and a photochromic layer. The anti-UV layer has an inner surface and an outer surface opposite to the inner surface. A UV light blocked by the anti-UV layer has a maximum wavelength that is defined as a first wavelength and is greater than or equal to 380 nm. The anti-fog layer is disposed on the inner surface of the anti-UV layer. The photochromic layer is disposed on the outer surface of the anti-UV layer. The photochromic layer has an adjustable transmittance that is changed when a UV light travels through the photochromic layer, and the anti-UV layer is configured to reflect a UV light traveling through the photochromic layer, back to the photochromic layer. The protective sheet is arranged adjacent to and spaced apart from the photochromic layer. A UV light blocked by the protective sheet has a maximum wavelength that is defined as a second wavelength and is less than or equal to 380 nm. The protective sheet is defined as an external view region and an external combining region that is in a ring shape and is arranged around the external view region. The combining layer connects the internal combining region of the multi-layer sheet and the external combining region of the protective sheet, thereby fixing the relative position of the multi-layer sheet and the protective sheet. The internal view region of the multi-layer sheet, the external view region of the protective sheet, and the combining layer are substantially sealed to jointly define an air layer. The air layer is configured to slow down the transference of an outer temperature of the protective sheet to the multi-layer sheet. The spectacle frame is fastened to a periphery portion of the composite lens. The internal combining region of the multi-layer sheet, the external combining region of the protective sheet, and the combining layer are fixed on the spectacle frame.

The present disclosure also provides a composite lens, which includes a multi-layer sheet, a protective sheet, and a combining layer. The multi-layer sheet is defined as an internal view region and an internal combining region that is in a ring shape and is arranged around the internal view region. The multi-layer sheet includes an anti-UV layer, an anti-fog layer, and a photochromic layer. The anti-UV layer has an inner surface and an outer surface opposite to the inner surface. A UV light blocked by the anti-UV layer has a maximum wavelength that is defined as a first wavelength and is greater than or equal to 380 nm. The anti-fog layer is disposed on the inner surface of the anti-UV layer. The photochromic layer is disposed on the outer surface of the anti-UV layer. The photochromic layer has an adjustable transmittance that is changed when a UV light travels through the photochromic layer. The anti-UV layer is configured to reflect a UV light traveling through the photochromic layer, back to the photochromic layer. The protective sheet is arranged adjacent to and spaced apart from the photochromic layer. A UV light blocked by the protective sheet has a maximum wavelength that is defined as a second wavelength and is less than or equal to 380 nm. The protective sheet is defined as an external view region and an external combining region that is in a ring shape and is arranged around the external view region. The combining layer connects the internal combining region of the multi-layer sheet and the external combining region of the protective sheet, thereby fixing the relative position of the multi-layer sheet and the protective sheet. The internal view region of the multi-layer sheet, the external view region of the protective sheet, and the combining layer are substantially sealed to jointly define an air layer. The air layer is configured to slow down the transference of an outer temperature of the protective sheet to the multi-layer sheet.

In summary, each of the snow goggle device and the composite lens of the present disclosure adapts the combining layer to connect the multi-layer sheet and the protective sheet so as to form the air layer, such that the components of the composite lens can cooperate with each other to increase the performance of the composite lens (e.g., the multi-layer structure of the composite lens can block an outer temperature for a better anti-fog effect; the air layer is formed to prevent the multi-layer sheet from undergoing a rapid temperature change that affects the photochromic sensitivity of the photochromic layer; the anti-UV layer is configured to reflect a UV light traveling through the photochromic layer, back to the photochromic layer, thereby effectively increasing the photochromic sensitivity of the photochromic layer). Specifically, the multi-layer structure of the composite lens can provide a better anti-fog effect for the anti-fog layer, and can provide a better photochromic sensitivity for the photochromic layer so as to rapidly change color.

In addition, for each of the snow goggle device and the composite lens of the present disclosure, the photochromic layer can be exposed in the air layer and not covered by other structures, such that the composite lens can have a better perspective rate.

In order to further appreciate the characteristics and technical contents of the present disclosure, references are hereunder made to the detailed descriptions and appended drawings in connection with the present disclosure. However, the appended drawings are merely shown for exemplary purposes, and should not be construed as restricting the scope of the present disclosure.

DETAILED DESCRIPTION OF THE EXEMPLARY EMBODIMENTS

References are hereunder made to the detailed descriptions and appended drawings in connection with the present disclosure. However, the appended drawings are merely provided for exemplary purposes, and should not be construed as restricting the scope of the present disclosure.

Figure 1:
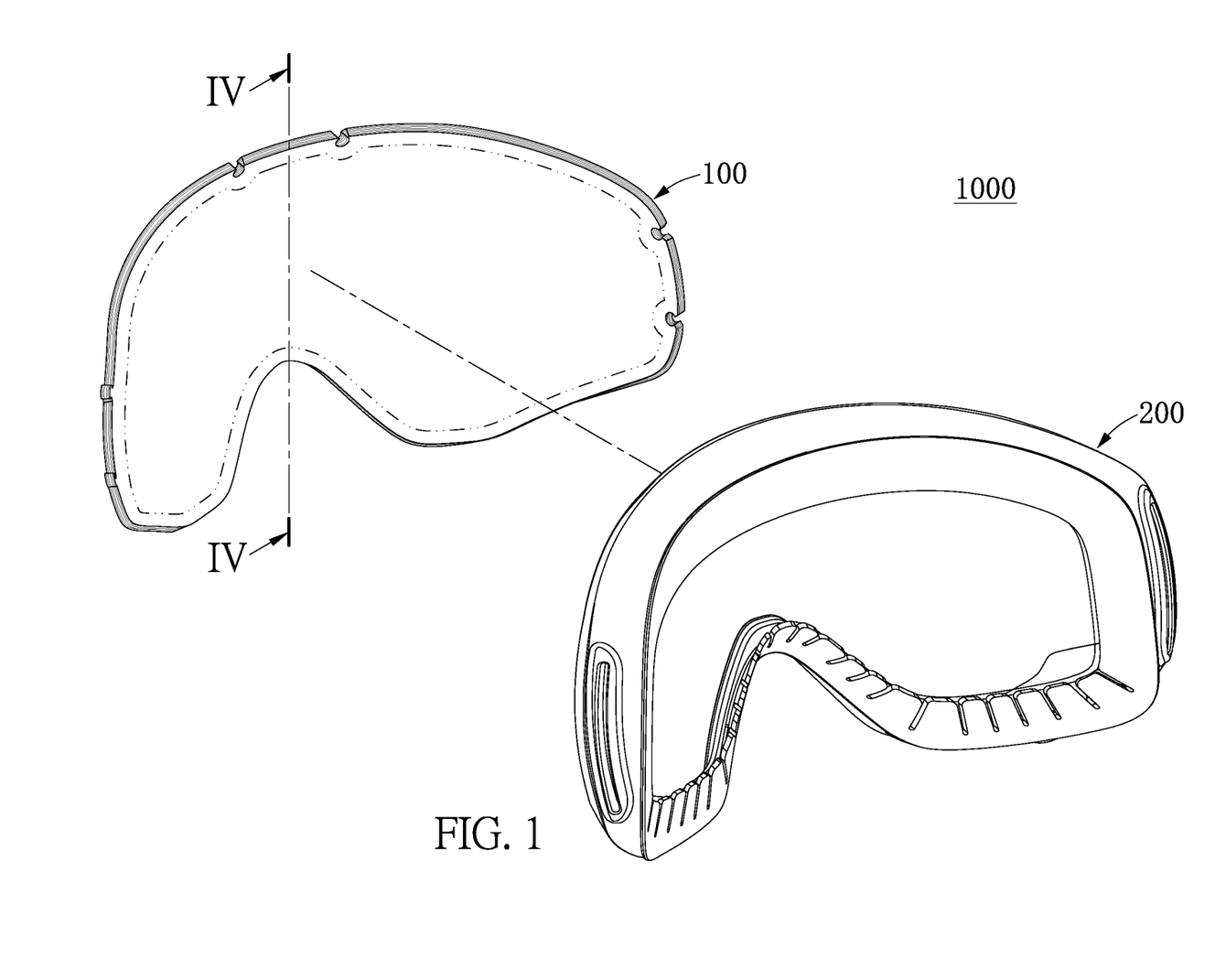
FIG. 1 is an exploded view showing a snow goggle device according to the present disclosure.

Reference is made to FIGS. 1 to 5, which illustrate an embodiment of the present disclosure. As shown in FIG. 1, the present embodiment discloses a snow goggle device 1000 used for being worn on (e.g., substantially and gaplessly attached to) a user's face, thereby protecting the user's eyes. In order to more easily describe the snow goggle device 1000 of the present embodiment, a side of the snow goggle device 1000 (e.g., the right side of the snow goggle device 1000 as shown in FIG. 1) close to the user's face is defined as an internal side, and an opposite side of the snow goggle device 1000 (e.g., the left side of the snow goggle device 1000 as shown in FIG. 1) away from the user's face is defined as an external side.

Figure 2:
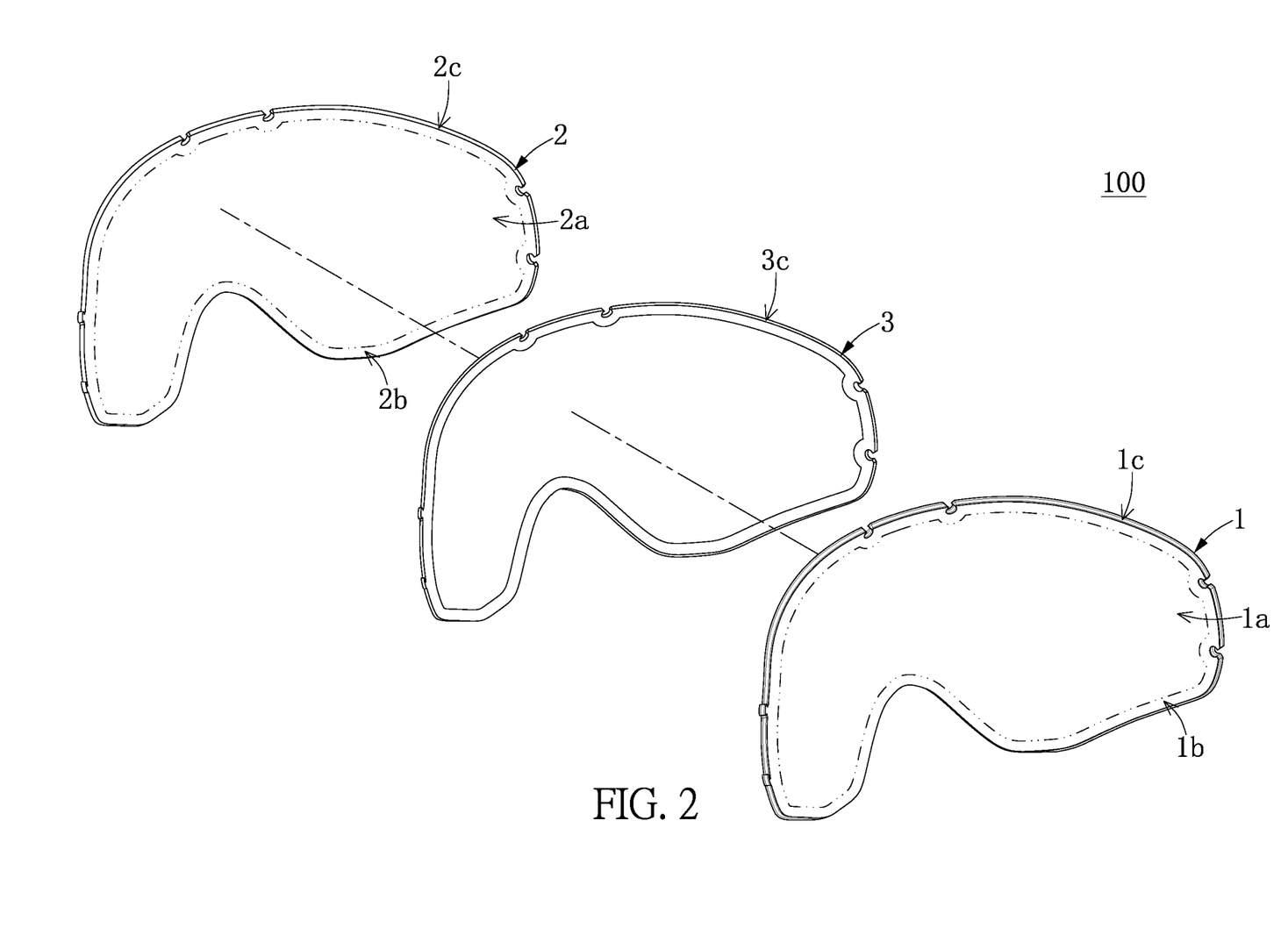
FIG. 2 is a first exploded view showing a composite lens of the snow goggle device according to the present disclosure.
Figure 3:
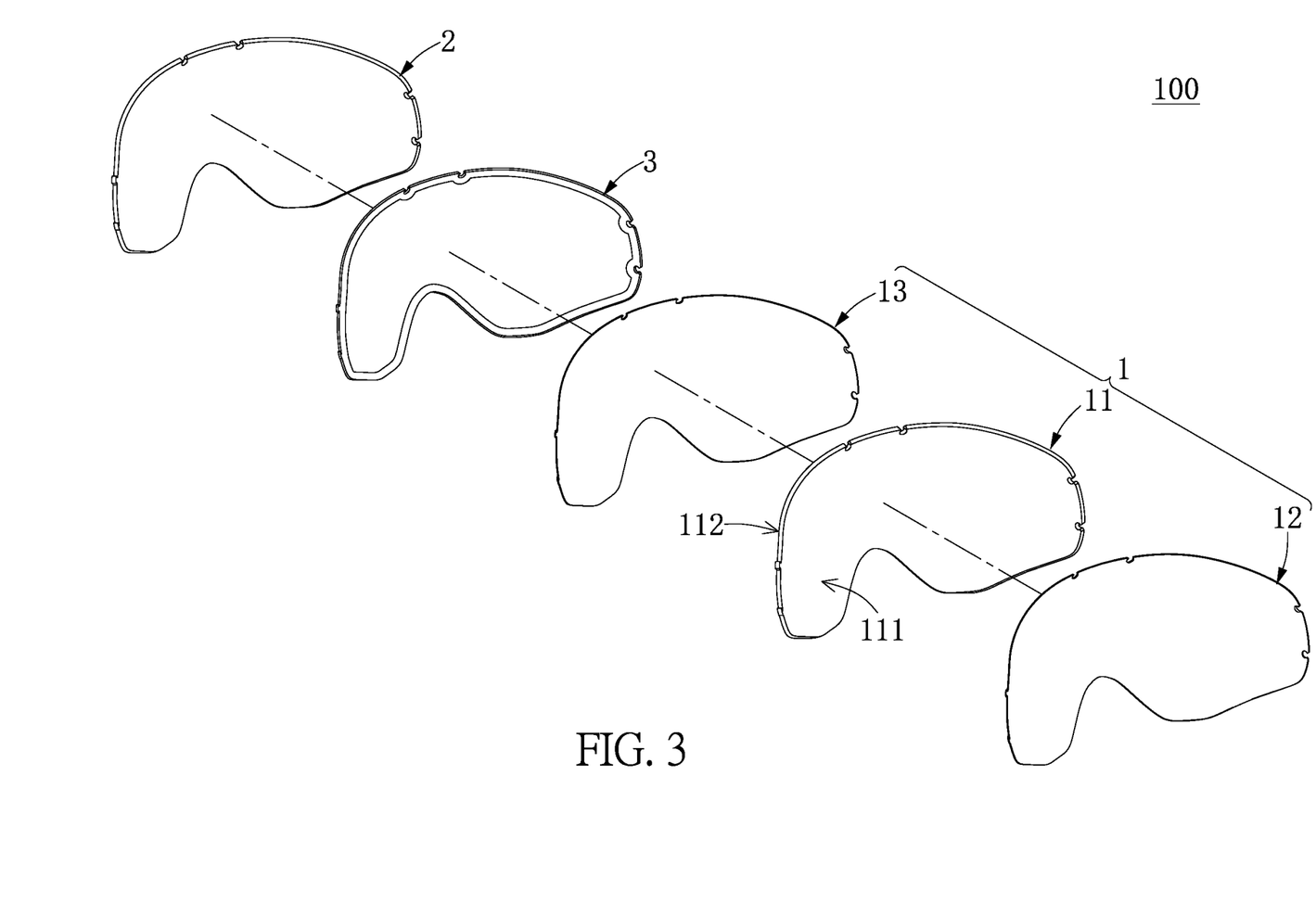
FIG. 3 is a second exploded view showing the composite lens of the snow goggle device according to the present disclosure.
Figure 4:
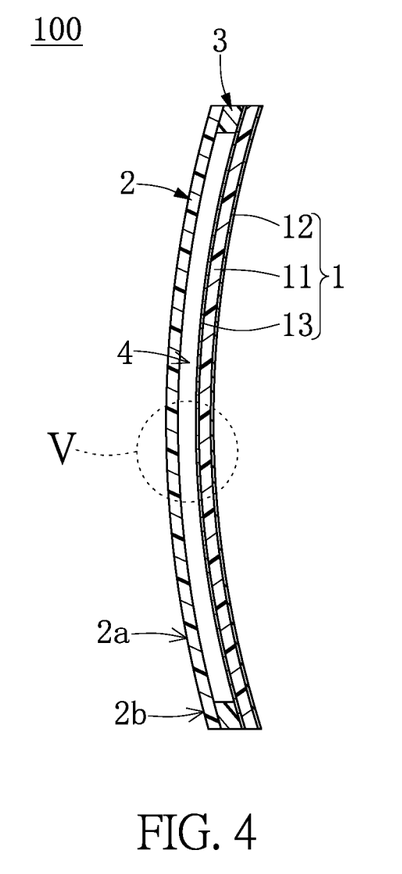
FIG. 4 is a cross-sectional view taken along a cross-section line IV-IV of FIG. 1.
Figure 5:
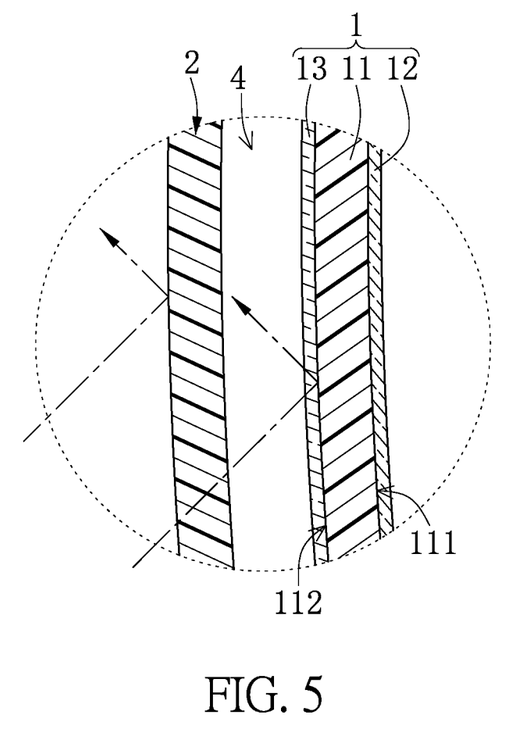
FIG. 5 is an enlarged view showing a V portion of FIG. 4.

As shown in FIGS. 1 and 2, the snow goggle device 1000 includes a composite lens 100 and a spectacle frame 200 fastened to (e.g., being sleeved around) a periphery portion of the composite lens 100. It should be noted that the composite lens 100 in the present embodiment is applied in the snow goggle device 1000, but the present disclosure is not limited thereto. For example, in other embodiments of the present disclosure, the composite lens 100 can be applied individually or applied to other devices different from the snow goggle device 1000. The following description discloses the structure and connection relationship of each of the composite lens 100 and the spectacle frame 200.

The composite lens 100 includes a multi-layer sheet 1, a protective sheet 2 spaced apart from the multi-layer sheet 1, and a combining layer 3 connecting the multi-layer sheet 1 and the protective sheet 2. Each of the multi-layer sheet 1 and the protective sheet 2 is in a curved shape, and the multi-layer sheet 1 is substantially parallel to the protective sheet 2. Moreover, in the present embodiment, an edge 1c of the multi-layer sheet 1, an edge 2c of the protective sheet 2, and an edge 3c of the combining layer 3 are substantially aligned with each other, but the present disclosure is not limited thereto.

As shown in FIGS. 2 to 5, the multi-layer sheet 1 is light-permeable, and the multi-layer sheet 1 includes an anti-UV layer 11, an anti-fog layer 12 disposed on the an inner surface 111 of the anti-UV layer 11, and a photochromic layer 13 disposed on an outer surface 112 of the anti-UV layer 11.

The anti-UV layer 11 in the present embodiment is not only used for blocking a UV light, but also used as a substrate for carrying the anti-fog layer 12 and the photochromic layer 13. Specifically, a thickness of the anti-UV layer 11 is preferably greater than that of the anti-fog layer 12, and is also greater than that of the photochromic layer 13, but the present disclosure is not limited thereto.

In the present embodiment, a UV light blocked by the anti-UV layer 11 has a maximum wavelength that is defined as a first wavelength and is greater than or equal to 380 nm (e.g., 400 nm or 420 nm). That is to say, the anti-UV layer 11 is configured to block or reflect a UV light having a wavelength less than or equal to the first wavelength (e.g., 380 nm).

Moreover, the material of the anti-UV layer 11 includes a polycarbonate (PC), a polypropylene (PP), a NXT, or a polyethylene terephthalate (PET), but the present disclosure is not limited thereto. Specifically, the material of the anti-UV layer 11 in the present embodiment includes PC.

The anti-fog layer 12 is a portion of the composite lens 100 arranged closest to the user's face, and is configured to prevent fog from being formed thereon. In the present embodiment, the anti-fog layer 12 can be directly formed on the inner surface 111 of the anti-UV layer 11 by injection molding or a hot pressing, or the anti-fog layer 12 can be seamlessly adhered to the inner surface 111 of the anti-UV layer 11. Moreover, the inner surface 111 of the anti-UV layer 11 in the present embodiment is entirely covered by the anti-fog layer 12, but the present disclosure is not limited thereto.

Specifically, the material of the anti-fog layer 12 in the present embodiment includes a cellulose acetate (CA), a cellulose propionate (CP), or a tri-cellulose acetate (TAC), but the present disclosure is not limited thereto.

The photochromic layer 13 has an adjustable transmittance that is changed when a UV light travels through the photochromic layer 13. In other words, when the photochromic layer 13 is located in a UV light environment, the color of the photochromic layer 12 gradually becomes deeper, and the transmittance of the photochromic layer 12 gradually reduces. When the photochromic layer 13 is located outside of the UV light environment, the transmittance of the photochromic layer 12 gradually increases to an initial value. Moreover, the anti-UV layer 11 is configured to reflect a UV light traveling through the photochromic layer 13, back to the photochromic layer 13, thereby effectively increasing a photochromic sensitivity of the photochromic layer 13.

In the present embodiment, the photochromic layer 13 can be directly formed on the outer surface 112 of the anti-UV layer 11 by coating or soaking, and the outer surface 112 of the anti-UV layer 11 is entirely covered by the photochromic layer 13, but the present embodiment is not limited thereto.

The protective sheet 2 is light-permeable, and is arranged adjacent to and spaced apart from the photochromic layer 13. The material of the protective sheet 2 includes PC, PP, NXT, or PET, but the present disclosure is not limited thereto. Specifically, the material of the protective sheet 2 in the present embodiment includes PC.

The protective sheet 2 in the present embodiment is provided for protecting the multi-layer sheet 1. In the present embodiment, a UV light blocked by the protective sheet 2 has a maximum wavelength that is defined as a second wavelength and is less than or equal to 380 nm (e.g., 350 nm, 320 nm, 300 nm, or 280 nm). That is to say, the protective sheet 2 is configured to block or reflect a UV light having a wavelength less than or equal to the second wavelength (e.g., 380 nm). It should be noted that the second wavelength can be 0 nm. In other words, the protective sheet 2 is not formed for blocking or reflecting any UV light.

Specifically, the first wavelength corresponding to the anti-UV layer 11 in the present embodiment is greater than the second wavelength corresponding to the protective sheet 2, and a difference between the first wavelength and the second wavelength is preferably less than or equal to 80 nm (e.g., 50 nm or 20 nm), but the present disclosure is not limited thereto.

Accordingly, a UV light received by the photochromic layer 13 in the present embodiment has a wavelength preferably within a range corresponding to the difference (e.g., 300 nm-380 nm). In other words, the difference between the first wavelength (e.g., 380 nm) and the second wavelength (e.g., 300 nm) can be adjusted according to the wavelength of the UV light received by the photochromic layer 13 (e.g., the photochromic layer 13 made of a photochromic dyes can receive a UV light having a wavelength within a range of 280 nm-380 nm), thereby effectively increasing the photochromic sensitivity of the photochromic layer 13, but the present disclosure is not limited thereto.

The protective sheet 2 is defined as an external view region 2a and an external combining region 2b that is in a ring shape and is arranged around the external view region 2a. The volume of the external view region 2a is at least 90% of the volume of the protective sheet 2. Moreover, the multi-layer sheet 1 is defined as an internal view region 1a and an internal combining region 1b that is in a ring shape and is arranged around the internal view region 1a. The volume of the internal view region 1a is at least 90% of the volume of the multi-layer sheet 1.

The combining layer 3 connects the internal combining region 1b of the multi-layer sheet 1 and the external combining region 2b of the protective sheet 2, thereby fixing the relative position of the multi-layer sheet 1 and the protective sheet 2. In the present embodiment, the combining layer 3 is preferably made of a material (e.g., an adhesive agent or an adhesive strip) having a high hermeticity, but the present disclosure is not limited thereto.

Moreover, the internal view region 1a of the multi-layer sheet 1, the external view region 2a of the protective sheet 2, and the combining layer 3 are substantially sealed to jointly define an air layer 4. In other words, a space surroundingly defined by the internal view region 1a, the external view region 2a, and the combining layer 3 is fully filled with air so as to form the air layer 4. Therefore, the air layer 4 is configured to slow down the transference of an outer temperature of the protective sheet 2 to the multi-layer sheet 1, thereby preventing the protective sheet 2 from undergoing a rapid temperature change that easily generates fog, or preventing the multi-layer sheet 1 from undergoing a rapid temperature change that affects the photochromic sensitivity of the photochromic layer 13.

In addition, the photochromic layer 13 in the present embodiment is preferably exposed in the air layer 4, and is not covered by other structures, such that the composite lens 100 can have a better perspective rate, but the present disclosure is not limited thereto. For example, in other embodiments of the present disclosure, a surface of the photochromic layer 13 arranged away from the anti-UV layer 11 can be further covered with an anti-fog layer.

Moreover, since light received by the user's eyes needs to travel through the internal view region 1a of the multi-layer sheet 1, the anti-fog layer 12 can be disposed only on a portion of the inner surface 111 of the anti-UV layer 11 corresponding in position to the internal view region 1a, and the photochromic layer 13 can be disposed only on a portion of the outer surface 112 of the anti-UV layer 11 corresponding in position to the internal view region 1a.

The composite lens 100 of the present embodiment has been disclosed in the above description, and the following description discloses the connection relationship between the composite lens 100 and the spectacle frame 200. The internal combining region 1b of the multi-layer sheet 1, the external combining region 2b of the protective sheet 2, and the combining layer 3 are fixed on the spectacle frame 200.

Specifically, the internal combining region 1b of the multi-layer sheet 1, the external combining region 2b of the protective sheet 2, and the combining layer 3 are substantially embedded in the spectacle frame 200, such that the spectacle frame 200 presses the internal combining region 1b and the external combining region 2b to abut against the combining layer 3 for firmly combining the components of the composite lens 100. In other embodiments of the present disclosure, the internal combining region 1b of the multi-layer sheet 1, the external combining region 2b of the protective sheet 2, and the combining layer 3 can be engaged with the spectacle frame 200.

Technical Effects of the Present Embodiments

In summary, each of the snow goggle device and the composite lens of the present disclosure adapts the combining layer to connect the multi-layer sheet and the protective sheet so as to form the air layer, such that the components of the composite lens can cooperate with each other to increase the performance of the composite lens (e.g., the multi-layer structure of the composite lens can block an outer temperature for having a better anti-fog effect; the air layer is formed to prevent the multi-layer sheet from undergoing a rapid temperature change that affects the photochromic sensitivity of the photochromic layer; the anti-UV layer is configured to reflect a UV light traveling through the photochromic layer, back to the photochromic layer, thereby effectively increasing the photochromic sensitivity of the photochromic layer). Specifically, the multi-layer structure of the composite lens can provide a better anti-fog effect for the anti-fog layer, and can provide a better photochromic sensitivity for the photochromic layer so as to rapidly change color.

Moreover, for each of the snow goggle device and the composite lens of the present disclosure, the first wavelength corresponding to the anti-UV layer is greater than the second wavelength corresponding to the protective sheet (e.g., a difference between the first wavelength and the second wavelength is less than or equal to 80 nm), such that the photochromic layer can receive a UV light traveling through the protective sheet and a UV light reflected from the anti-UV layer, effectively increasing the photochromic sensitivity of the photochromic layer.

Furthermore, for each of the snow goggle device and the composite lens of the present disclosure, the difference (e.g., 80 nm) between the first wavelength (e.g., 380 nm) and the second wavelength (e.g., 300 nm) can be adjusted according to the wavelength of the UV light received by the photochromic layer (e.g., the photochromic layer made of a photochromic dyes can receive a UV light having a wavelength within a range of 280 nm-380 nm), thereby effectively increasing the photochromic sensitivity of the photochromic layer.

In addition, for each of the snow goggle device and the composite lens of the present disclosure, the photochromic layer can be exposed in the air layer and is not covered by other structures, such that the composite lens can have a better perspective rate.

The descriptions illustrated supra set forth simply the exemplary embodiments of the present disclosure; however, the characteristics of the present disclosure are by no means restricted thereto. All changes, alterations, or modifications conveniently considered by those skilled in the art are deemed to be encompassed within the scope of the present disclosure delineated by the following claims.

What is claimed is:

1. A snow goggle device, comprising:
    a composite lens including:
        a multi-layer sheet defined as an internal view region and an internal combining region that is in a ring shape and is arranged around the internal view region, the multi-layer sheet including:
            an anti-UV layer having an inner surface and an outer surface opposite to the inner surface, wherein a UV light blocked by the anti-UV layer has a maximum wavelength that is defined as a first wavelength and is greater than or equal to 380 nm;
            an anti-fog layer disposed on the inner surface of the anti-UV layer; and
            a photochromic layer disposed on the outer surface of the anti-UV layer, wherein the photochromic layer has an adjustable transmittance that is changed when a UV light travels through the photochromic layer, and the anti-UV layer is configured to reflect a UV light traveling through the photochromic layer back to the photochromic layer;
        a protective sheet arranged adjacent to and spaced apart from the photochromic layer, wherein a UV light blocked by the protective sheet has a maximum wavelength that is defined as a second wavelength and is less than or equal to 380 nm, and wherein the protective sheet is defined as an external view region and an external combining region that is in a ring shape and is arranged around the external view region; and
        a combining layer connecting the internal combining region of the multi-layer sheet and the external combining region of the protective sheet, thereby fixing the relative position of the multi-layer sheet and the protective sheet,
        wherein the internal view region of the multi-layer sheet, the external view region of the protective sheet, and the combining layer are substantially sealed to jointly define an air layer, and the air layer is configured to slow down the transference of an outer temperature of the protective sheet to the multi-layer sheet; and
    a spectacle frame fastened to a periphery portion of the composite lens, wherein the internal combining region of the multi-layer sheet, the external combining region of the protective sheet, and the combining layer are fixed on the spectacle frame.

2. The snow goggle device as claimed in claim 1, wherein the material of at least one of the anti-UV layer and the protective sheet includes a polycarbonate (PC), a polypropylene (PP), a NXT, or a polyethylene terephthalate (PET).

3. The snow goggle device as claimed in claim 1, wherein the material of the anti-fog layer includes a cellulose acetate (CA), a cellulose propionate (CP), or a tri-cellulose acetate (TAC), and wherein the anti-fog layer is directly formed on or adhered to the inner surface of the anti-UV layer.

4. The snow goggle device as claimed in claim 1, wherein each of the multi-layer sheet and the protective sheet is in a curved shape, the inner surface of the anti-UV layer is entirely covered by the anti-fog layer, the outer surface of the anti-UV layer is entirely covered by the photochromic layer, and the anti-UV layer is substantially parallel to the protective sheet.

5. The snow goggle device as claimed in claim 1, wherein an edge of the multi-layer sheet, an edge of the protective sheet, and an edge of the combining layer are substantially aligned with each other.

6. The snow goggle device as claimed in claim 1, wherein the second wavelength is 0 nm.

7. The snow goggle device as claimed in claim 1, wherein a difference between the first wavelength and the second wavelength is less than or equal to 80 nm.

8. A composite lens, comprising:
    a multi-layer sheet defined as an internal view region and an internal combining region that is in a ring shape and is arranged around the internal view region, the multi-layer sheet including:
        an anti-UV layer having an inner surface and an outer surface opposite to the inner surface, wherein a UV light blocked by the anti-UV layer has a maximum wavelength that is defined as a first wavelength and is greater than or equal to 380 nm;
        an anti-fog layer disposed on the inner surface of the anti-UV layer; and
        a photochromic layer disposed on the outer surface of the anti-UV layer, wherein the photochromic layer has an adjustable transmittance that is changed when a UV light travels through the photochromic layer, and the anti-UV layer is configured to reflect a UV light traveling through the photochromic layer back to the photochromic layer;
    a protective sheet arranged adjacent to and spaced apart from the photochromic layer, wherein a UV light blocked by the protective sheet has a maximum wavelength that is defined as a second wavelength and is less than or equal to 380 nm, and wherein the protective sheet is defined as an external view region and an external combining region that is in a ring shape and is arranged around the external view region; and
    a combining layer connecting the internal combining region of the multi-layer sheet and the external combining region of the protective sheet, thereby fixing the relative position of the multi-layer sheet and the protective sheet,
    wherein the internal view region of the multi-layer sheet, the external view region of the protective sheet, and the combining layer are substantially sealed to jointly define an air layer, and the air layer is configured to slow down the transference of an outer temperature of the protective sheet to the multi-layer sheet.

9. The composite lens as claimed in claim 8, wherein the second wavelength is 0 nm.

10. The composite lens as claimed in claim 8, wherein a difference between the first wavelength and the second wavelength is less than or equal to 80 nm.

* * * * *